(12) United States Patent
Nemec et al.

(10) Patent No.: US 11,375,954 B2
(45) Date of Patent: Jul. 5, 2022

(54) CATHETER WITH VARIABLE RADIUS LOOP

(71) Applicant: St. Jude Medical, Cardiology Division, Inc., St. Paul, MN (US)

(72) Inventors: Linda Kay Nemec, Andover, MN (US); Fos Ulus Kuehn, Richfield, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 479 days.

(21) Appl. No.: 16/339,964

(22) PCT Filed: Oct. 20, 2017

(86) PCT No.: PCT/US2017/057655
§ 371 (c)(1),
(2) Date: Apr. 5, 2019

(87) PCT Pub. No.: WO2018/085062
PCT Pub. Date: May 11, 2018

(65) Prior Publication Data
US 2019/0282172 A1    Sep. 19, 2019

Related U.S. Application Data

(60) Provisional application No. 62/415,797, filed on Nov. 1, 2016.

(51) Int. Cl.
*A61B 5/00* (2006.01)
*A61B 18/14* (2006.01)
*A61B 5/287* (2021.01)
*A61B 18/00* (2006.01)

(52) U.S. Cl.
CPC ............ *A61B 5/6856* (2013.01); *A61B 5/287* (2021.01); *A61B 18/1492* (2013.01);
(Continued)

(58) Field of Classification Search
CPC ... A61B 5/6856; A61B 5/287; A61B 18/1492; A61B 2018/00375; A61B 2018/00577;
(Continued)

(56) References Cited

U.S. PATENT DOCUMENTS 5,827,272 A   10/1998  Breining et al.
6,602,248 B1   8/2003  Sharps et al.
(Continued)

FOREIGN PATENT DOCUMENTS

JP    07-088093     4/2007
JP    2011-045720   3/2011
(Continued)

OTHER PUBLICATIONS

Written Opinion and International Search Report for PCT/US2017/057655, dated Dec. 21, 2017.
(Continued)

*Primary Examiner* — Eun Hwa Kim
(74) *Attorney, Agent, or Firm* — Wiley Rein LLP

(57) ABSTRACT

A catheter includes a body having a proximal region that extends along a longitudinal axis, a distal region predisposed into a loop via shaping wire, and a neck region between the proximal and distal regions. The loop is disposed in a plane generally orthogonal to the longitudinal axis. An activation wire is coupled to the distal region and to an actuator in a manner that allows a user to adjust the radius of the loop. The activation and shaping wires are contained within a tube-shaped constraint, such as a spring coil, within the neck in order to the neck from nodding when the activation wire is activated.

20 Claims, 3 Drawing Sheets

(52) U.S. Cl.
CPC .............. *A61B 2018/00375* (2013.01); *A61B 2018/00577* (2013.01); *A61B 2018/00839* (2013.01); *A61B 2018/1407* (2013.01); *A61B 2018/1435* (2013.01); *A61B 2562/0209* (2013.01)

(58) Field of Classification Search
CPC .. A61B 2018/00839; A61B 2018/1407; A61B 2018/1435; A61B 2562/0209
USPC ........................................................ 600/374
See application file for complete search history.

(56) References Cited

U.S. PATENT DOCUMENTS

| | | | | |
|---|---|---|---|---|
| 7,606,609 | B2 * | 10/2009 | Muranushi | A61B 5/287 600/374 |
| 8,369,923 | B2 | 2/2013 | de la Rama et al. | |
| 2005/0010095 | A1 | 1/2005 | Stewart et al. | |
| 2011/0257499 | A1 * | 10/2011 | de la Rama | A61B 5/287 600/373 |
| 2016/0114132 | A1 * | 4/2016 | Chmielewski | A61B 5/6857 604/95.04 |
| 2016/0136389 | A1 | 5/2016 | Christian et al. | |

FOREIGN PATENT DOCUMENTS

| | | |
|---|---|---|
| JP | 2011-224364 | 11/2011 |
| JP | 2016-097307 | 5/2016 |

OTHER PUBLICATIONS

EP Communication for Application No. 17 801 530.1, dated Dec. 20, 2019.

* cited by examiner

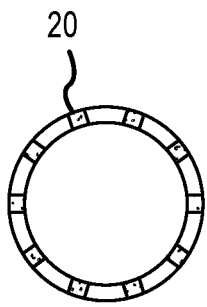
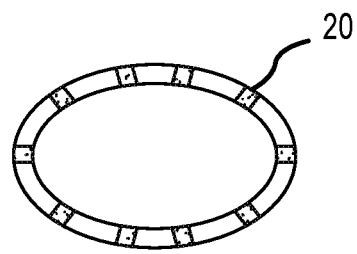
FIG.2B  FIG.3B
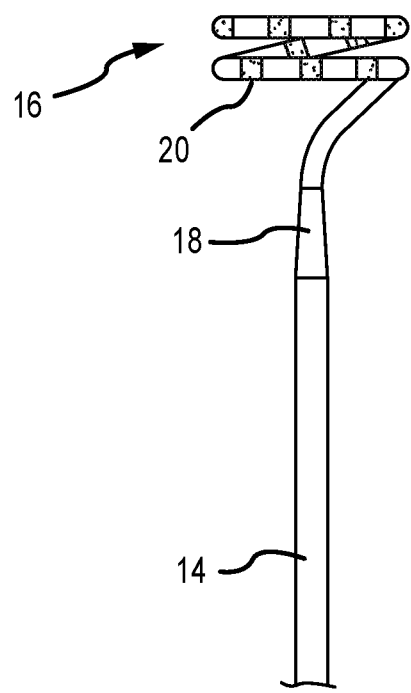
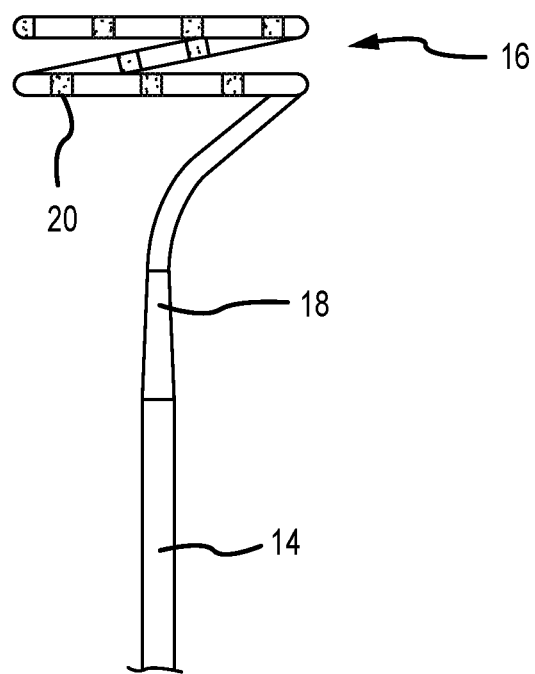
FIG.2A  FIG.3A

CATHETER WITH VARIABLE RADIUS LOOP

CROSS-REFERENCE TO RELATED APPLICATIONS

This application claims the benefit of U.S. provisional application No. 62/415,797, filed 1 Nov. 2016, which is hereby incorporated by reference as though fully set forth herein.

BACKGROUND

The instant disclosure relates to catheters for use in medical procedures, such as electrophysiology studies. In particular, the instant disclosure relates to a catheter for use in diagnostic and therapeutic procedures at or near an annular region of a patient's anatomy, such as the ostium of a pulmonary vein.

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart.

A typical electrophysiology catheter includes an elongate shaft and one or more electrodes on the distal end of the shaft. The electrodes may be used for ablation, diagnosis, or the like. Oftentimes, these electrodes are ring electrodes that extend about the entire circumference of the catheter shaft.

One specific use of an electrophysiology catheter is to map the atrial regions of the heart, and in particular the pulmonary veins, which are often origination points or foci of atrial fibrillation. Such electrophysiology mapping catheters typically have at least a partial loop shape at their distal end, oriented in a plane generally orthogonal to the longitudinal axis of the catheter shaft, which allows the loop to surround the pulmonary vein ostia.

Because of varying patient anatomies, however, it may be challenging to properly place the looped section of the catheter precisely in the pulmonary vein ostia. Thus, many extant catheters are configured such that the loop portion has a variable radius that can be adjusted via a control handle attached to the proximal end of the catheter shaft. Occasionally, however, adjusting the radius of the loop portion will have the unintended consequence of causing the "neck" of the catheter (i.e., where the catheter transitions from a relatively straight proximal section to the looped distal section) to "nod" (i.e., deflect the plane in which the loop lies relative to the relatively straight proximal section of the catheter shaft).

BRIEF SUMMARY

Disclosed herein is a catheter including: a catheter body having a proximal region, a neck region, and a distal region predisposed into at least a partial loop disposed in a plane; a handle joined to the proximal region and including an actuator; an activation wire coupled to the actuator and to the distal region such that, when a user actuates the actuator, the activation wire is activated to cause the at least a partial loop of the distal region to vary in radius; and a tube-shaped constraint within the neck that prevents nodding of the neck when the activation wire is activated. The catheter can also include a plurality of electrodes disposed on the distal region.

According to aspects of the instant disclosure, the catheter further includes a shape memory wire extending through the neck and at least a portion of the distal region and shaping the portion of the distal region into the at least a partial loop. Both the activation wire and the shape memory wire can be constrained within the constraint. In embodiments, an inner diameter of the constraint is no more than 0.003" greater than a combined thickness of the activation wire and the shape memory wire; in other embodiments, the inner diameter of the constraint is no more than 0.002" greater than the combined thickness of the activation wire and the shape memory wire.

The constraint can be a rigid tube, a metallic tube, or a compression coil, such as a coil spring or a wound round wire having a diameter of about 0.002". The constraint also has an overall length. In embodiments, about 40% of the overall length of the constraint can extend parallel to the proximal region of the catheter body, while about 60% of the overall length of the constraint can lie in the plane of the distal region of the catheter body.

Also disclosed herein is a catheter including: a catheter body having a proximal region that extends along an axis, a distal region predisposed into at least a partial loop disposed in a plane orthogonal to the axis of the proximal region, and a neck region between the proximal region and the distal region; a handle joined to the proximal region and including an actuator; an activation wire coupled to the actuator and to the distal region such that, when a user actuates the actuator, the activation wire is activated to cause the at least a partial loop of the distal region to vary in radius; a shape memory wire extending through the neck region and at least a portion of the distal region to shape the portion of the distal region into the at least a partial loop; and an undeformable constraint within the neck region, wherein the activation wire and the shape memory wire are positioned within the undeformable constraint. It is contemplated that the undeformable constraint can permit the distal region of the catheter body to nod relative to the proximal region of the catheter body by up to ten degrees relative to the axis of the proximal region of the catheter body. In embodiments, thus, the undeformable constraint can be a spring steel coil. An inner diameter of the undeformable constraint can also be no more than 0.003" greater than a combined thickness of the activation wire and the shape memory wire.

In embodiments of the disclosure, a first portion of the undeformable constraint can extend along the axis of the proximal region of the catheter body and a second portion of the undeformable constraint can extend within the plane of the distal region of the catheter body.

According to another aspect of the disclosure, a method of manufacturing a medical device includes the following steps: forming an elongate body having a distal region and a proximal region; disposing a shape memory wire within a distal region of the body to predispose the distal region of the body into at least a partial loop disposed in a plane, wherein the plane is orthogonal to an axis of the proximal region, thereby forming a neck region between the proximal region and the distal region; disposing an activation wire through the elongate body; securing the activation wire to the distal region; and forming an undeformable constraint about the shape memory wire and the activation wire within the neck region. The undeformable constraint can be formed about the shape memory wire and the activation wire within the neck region by surrounding the shape memory wire and the activation wire with a compression coil within the neck region. An inner diameter of the undeformable constraint can exceed a combined thickness of the shape memory wire and the activation wire by no more than 0.003".

The method can also include securing the proximal region of the elongate body to a handle including an actuator; and securing the activation wire to the actuator such that, when a user actuates the actuator, the activation wire is activated to cause the at least a partial loop of the distal region to vary in radius.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 2A is a close up of a portion of an electrophysiology catheter according to some embodiments of the instant disclosure.

FIG. 2B is an end view of the electrophysiology catheter of FIG. 2A.

FIG. 3A is a close up of a portion of an electrophysiology catheter according to additional embodiments of the instant disclosure.

FIG. 3B is an end view of the electrophysiology catheter of FIG. 3A.

DETAILED DESCRIPTION

For the sake of illustration, certain embodiments of the disclosure will be explained herein with reference to an electrophysiology catheter utilized in cardiac electrophysiology studies, such as the Inquiry™ Optima™ diagnostic catheter of St. Jude Medical, Inc. It should be understood, however, that the present teachings may be applied to good advantage in other contexts as well.

Figure 1:
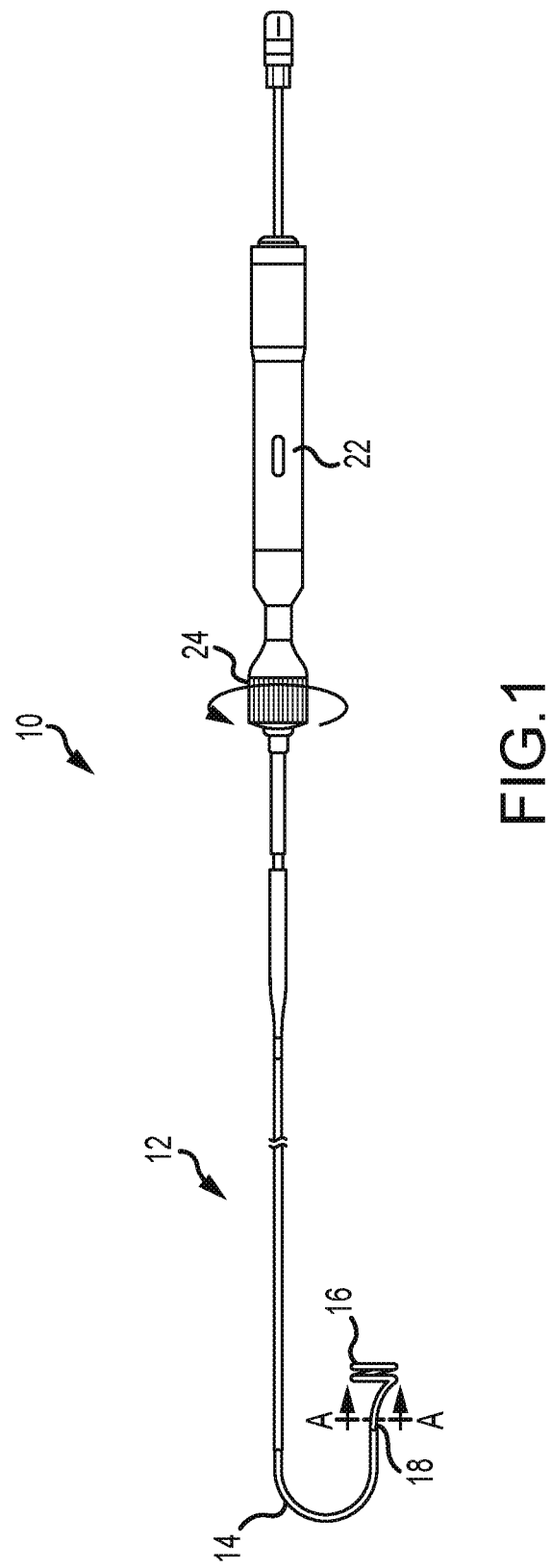
FIG. 1 illustrates an exemplary electrophysiology catheter.

Referring now to the figures, FIG. 1 depicts an electrophysiology ("EP") catheter 10 according to a first aspect of the present disclosure.

EP catheter 10 generally includes an elongate catheter body 12, which, in some embodiments, is tubular (e.g., it defines at least one lumen therethrough). Catheter body 12 includes a proximal region 14, a distal region 16, and a neck region 18 between proximal region 14 and distal region 16. The relative lengths of proximal region 14, distal region 16, and neck region 18 as depicted in FIG. 1 are merely illustrative and may vary without departing from the spirit and scope of the instant disclosure. Of course, the overall length of catheter body 12 should be long enough to reach the intended destination within the patient's body.

Catheter body 12 will typically be made of a biocompatible polymeric material, such as polytetrafluoroethylene (PTFE) tubing (e.g., TEFLON® brand tubing). Of course, other polymeric materials, such as fluorinated ethylene-propylene copolymer (FEP), perfluoroalkoxyethylene (PFA), poly(vinylidene fluoride), poly(ethylene-co-tetrafluoroethylene), and other fluoropolymers, may be utilized. Additional suitable materials for catheter body 12 include, without limitation, polyamide-based thermoplastic elastomers (namely poly(ether-block-amide), such as PEBAX®), polyester-based thermoplastic elastomers (e.g., HYTREL®), thermoplastic polyurethanes (e.g., PELLETHANE®, ESTANE®), ionic thermoplastic elastomers, functionalized thermoplastic olefins, and any combinations thereof. In general, suitable materials for catheter body 12 may also be selected from various thermoplastics, including, without limitation, polyamides, polyurethanes, polyesters, functionalized polyolefins, polycarbonate, polysulfones, polyimides, polyketones, liquid crystal polymers and any combination thereof. It is also contemplated that the durometer of catheter body 12 may vary along its length. In general, the basic construction of catheter body 12 will be familiar to those of ordinary skill in the art, and thus will not be discussed in further detail herein.

As seen in FIGS. 2A, 2B, 3A, and 3B, distal region 16 of catheter body 12 is predisposed into at least a partial loop. This loop shape allows distal region 16 to conform to the shape, for example, of a pulmonary vein ostium. The partial loop may take a number of configurations, depending on the intended or desired use of EP catheter 10, consistent with the present teachings. Therefore, it should be understood that the circular and elliptical loop configurations depicted in FIGS. 2B and 3B, respectively, are merely illustrative.

FIGS. 2A, 2B, 3A, and 3B also illustrate that distal region 16 can include a plurality of electrodes 20 disposed thereon. Electrodes 20 may be ring electrodes or any other electrodes suitable for a particular application of EP catheter 10. For example, where EP catheter 10 is intended for use in a contactless electrophysiology study, electrodes 20 may be configured as described in U.S. application Ser. No. 12/496,855, filed 2 Jul. 2009, which is hereby incorporated by reference as though fully set forth herein. Of course, in addition to serving sensing purposes (e.g., cardiac mapping and/or diagnosis), electrodes 20 may be employed for therapeutic purposes (e.g., cardiac ablation and/or pacing).

Referring again to FIG. 1, a handle 22 is coupled to proximal region 14 of catheter body 12. Handle 22 includes suitable actuators (e.g., knob 24) to control the deflection of catheter body 12, for example as described in U.S. Pat. No. 8,369,923, which is hereby incorporated by reference as though fully set forth herein. Various handles and their associated actuators for use in connection with electrophysiology catheters are known, and thus handle 22 will not be described in further detail herein.

It is contemplated that the radius of curvature of the loop of distal region 16 may be adjustable, for example to conform to the varying sizes of pulmonary vein ostia of patients of different ages. This additional control may be provided, for example, via the use of an activation wire 26, shown in FIG. 4, that is adapted to alter the radius of curvature of the loop of distal region 16. One suitable material for activation wire 26 is stainless steel, though other materials can be employed without departing from the spirit and scope of the instant disclosure.

In some embodiments, one end (e.g., the distal end) of activation wire 26 may be coupled to the tip of catheter body 12 (e.g., coupled to a distal-most tip electrode of electrodes 20), while the other end (e.g., the proximal end) of activation wire 26 may be coupled to an actuator (e.g., knob 24) on handle 22. Thus, for example, turning knob 24 can place activation wire 26 in tension, thereby altering the radius of curvature of the loop of distal region 16.

Another exemplary mechanism for varying the radius of curvature of the loop of distal region 16 is described in U.S. Pat. No. 7,606,609, which is hereby incorporated by reference as though fully set forth herein.

Figure 4:
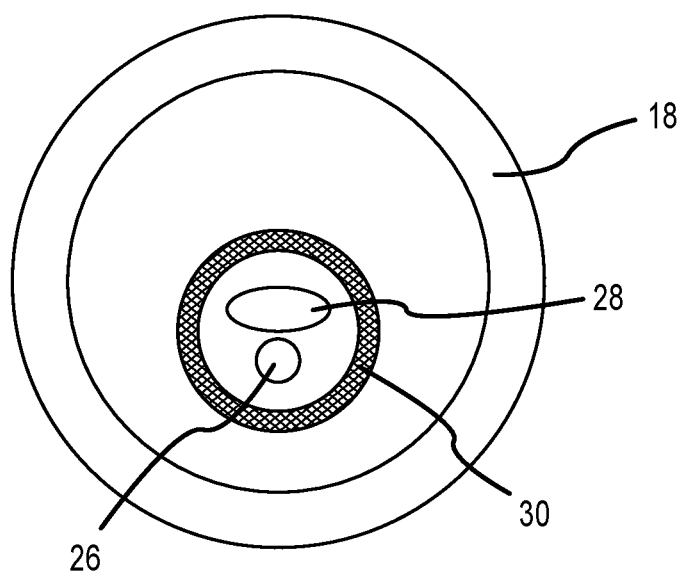
FIG. 4 is a transverse cross-section taken along line A-A in FIG. 1.

FIG. 4 also depicts a shaping wire 28. Shaping wire 28 extends through neck region 18 and at least partially through distal region 16 in order to help predispose distal region 16 into the loop shape depicted throughout the Figures. Shaping wire 28 can be made from a shape memory material such as nitinol.

Neck region 18 provides a transition from the relatively straight proximal region 14 to the plane of the distal region 16. Neck region 18 further includes a tube-shaped constraint 30. Constraint 30 surrounds at least a portion of activation wire 26. In embodiments, constraint 30 also surrounds at least a portion of shaping wire 28. Constraint 30 minimizes nodding of neck region 18 by keeping activation wire 26 and shaping wire 28 in close proximity to each other, particularly as tension is applied to activation wire 26 in order to vary the radius of curvature of the loop of distal region 16.

According to aspects of the disclosure, the inner diameter of constraint 30 is between about 0.002" and about 0.0003" greater than the combined thickness of activation wire 26 and shaping wire 28. Thus, for example, if activation wire 28 has a thickness (e.g. diameter) of about 0.008" and shaping wire 26 has a thickness of about 0.015", the inner diameter of constraint 30 can be between about 0.025" and 0.026".

The term "undeformable" is used herein to describe constraint 30. "Undeformable" as used herein, however, is not limited to a rigid or substantially rigid tube (though rigid and substantially rigid tubes are "undeformable" within the meaning of the instant disclosure). Rather, the term "undeformable" contemplates a certain degree of flexibility or malleability of constraint 30, and thus of neck region 18. In embodiments, constraint 30 allows neck region 18 to nod by no more than about 10 degrees relative to the longitudinal axis of catheter body 12.

To facilitate this certain degree of flexibility or malleability, in embodiments of the disclosure constraint 30 is a compression coil, such as a coil spring. Constraint 30 can be made by winding a round spring steel wire having a diameter of about 0.002" into a compression coil. In the exemplary embodiment described above, therefore, the outer diameter of constraint 30 would be between about 0.029" and 0.030".

The overall length of constraint 30 can be about half an inch. In embodiments, about 40% of the length of constraint 30 can follow the relatively straight proximal portion 14, while about 60% of the length of constraint can lie within the plane of distal region 16.

In use, EP catheter 10 is introduced into a patient's body proximate an area of interest, such as a pulmonary vein ostium. Of course, EP catheter 10 may be introduced surgically (e.g., via an incision in the patient's chest) or non-surgically (e.g., navigated through the patient's vasculature to a desired site, with or without the assistance of a sheath, guidewire, or the like). Once oriented, the practitioner can use actuator 24 to adjust the radius of curvature of the loop of distal region 16 to properly fit the patient's anatomy. Advantageously, due to constraint 30, neck region 18 will remain stable during these adjustments, mitigating the need to further reposition EP catheter 10 once the adjustments are complete. Electrodes 20 may then be employed for diagnostic and/or therapeutic purposes.

Although several embodiments of this invention have been described above with a certain degree of particularity, those skilled in the art could make numerous alterations to the disclosed embodiments without departing from the spirit or scope of this invention.

For example, it should be understood that the dimensions and configurations of constraint 30 described herein are merely exemplary.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter comprising:
   a catheter body having a proximal region, a neck region, and a distal region predisposed into at least a partial loop disposed in a plane;
   a handle joined to the proximal region and including an actuator;
   an activation wire coupled to the actuator, extending through the proximal region and neck region and into the at least a partial loop of the distal region, and coupled to the distal region such that, when a user actuates the actuator, the activation wire is activated to cause the at least a partial loop of the distal region to vary in radius;
   a shape memory wire, separate from the activation wire, extending through the neck and at least a portion of the distal region and shaping the portion of the distal region into the at least a partial loop; and
   a tube-shaped constraint within the neck, wherein the activation wire is detached from the shape memory wire and disposed within the tube-shaped constraint such that when tension is applied to the activation wire to vary the radius of the partial loop, the tube-shaped constraint prevents nodding of the neck by keeping the activation wire and the shaping wire in close proximity to each other.

2. The catheter according to claim 1, wherein the tube-shaped constraint comprises a rigid tube.

3. The catheter according to claim 1, wherein the tube-shaped constraint comprises a metallic tube.

4. The catheter according to claim 1, wherein the tube-shaped constraint comprises a compression coil.

5. The catheter according to claim 4, wherein the tube-shaped constraint comprises a coil spring.

6. The catheter according to claim 4, wherein the compression coil comprises a wound round wire having a diameter of 0.002".

7. The catheter according to claim 6, wherein an inner diameter of the constraint is no more than 0.003" greater than a combined thickness of the activation wire and the shape memory wire.

8. The catheter according to claim 7, wherein the inner diameter of the constraint is no more than 0.002" greater than the combined thickness of the activation wire and the shape memory wire.

9. The catheter according to claim 1, further comprising a plurality of electrodes disposed on the distal region.

10. The catheter according to claim 1, wherein the tube-shaped constraint has an overall length, and wherein 40% of the overall length of the constraint extends parallel to the proximal region of the catheter body and 60% of the overall length of the constraint lies in the plane of the distal region of the catheter body.

11. The catheter according to claim 1, wherein the shape memory wire and the activation wire are free to move relative to each other within the constraint.

12. A catheter comprising:
  a catheter body having a proximal region that extends along an axis, a distal region predisposed into at least a partial loop disposed in a plane orthogonal to the axis of the proximal region, and a neck region between the proximal region and the distal region;
  a handle joined to the proximal region and including an actuator;
  an activation wire coupled to the actuator, extending through the proximal region and neck region and into the at least a partial loop of the distal region, and coupled to the distal region such that, when a user actuates the actuator, the activation wire is activated to cause the at least a partial loop of the distal region to vary in radius;
  a shape memory wire, separate from the activation wire, extending through the neck region and at least a portion of the distal region to shape the portion of the distal region into the at least a partial loop; and
  an undeformable constraint within the neck region,
  wherein the activation wire is detached from the shape memory wire and the activation wire and the shape memory wire are positioned within the undeformable constraint such that when tension is applied to the activation wire to vary the radius of the partial loop, the undeformable constraint minimizes nodding of the neck by keeping the activation wire and the shaping wire in close proximity to each other.

13. The catheter according to claim 12, wherein the undeformable constraint permits the distal region of the catheter body to nod relative to the proximal region of the catheter body by up to ten degrees relative to the axis of the proximal region of the catheter body.

14. The catheter according to claim 12, wherein the undeformable constraint comprises a spring steel coil.

15. The catheter according to claim 12, wherein an inner diameter of the undeformable constraint is no more than 0.003" greater than a combined thickness of the activation wire and the shape memory wire.

16. The catheter according to claim 12, wherein a first portion of the undeformable constraint extends along the axis of the proximal region of the catheter body and a second portion of the undeformable constraint extends within the plane of the distal region of the catheter body.

17. A method of manufacturing a medical device, the method comprising:
  forming an elongate body having a distal region and a proximal region;
  disposing a shape memory wire within a distal region of the body to predispose the distal region of the body into at least a partial loop disposed in a plane, wherein the plane is orthogonal to an axis of the proximal region, thereby forming a neck region between the proximal region and the distal region;
  disposing an activation wire, separate from the shape memory wire, through the elongate body from the proximal region into the at least a partial loop of the distal region;
  securing the activation wire to the distal region; and
  forming an undeformable constraint about the shape memory wire and the activation wire within the neck region, wherein the shape memory wire and the activation wire are detached from each other within the neck region.

18. The method according to claim 17, wherein the step of forming an undeformable constraint about the shape memory wire and the activation wire within the neck region comprises surrounding the shape memory wire and the activation wire with a compression coil within the neck region.

19. The method according to claim 17, wherein an inner diameter of the undeformable constraint exceeds a combined thickness of the shape memory wire and the activation wire by no more than 0.003".

20. The method according to claim 17, further comprising:
  securing the proximal region of the elongate body to a handle including an actuator; and
  securing the activation wire to the actuator such that, when a user actuates the actuator, the activation wire is activated to cause the at least a partial loop of the distal region to vary in radius.

* * * * *